(12) United States Patent
Haruki et al.

(10) Patent No.: US 11,437,001 B2
(45) Date of Patent: Sep. 6, 2022

(54) IMAGE PROCESSING APPARATUS, PROGRAM AND IMAGE PROCESSING METHOD

(71) Applicant: EIZO Corporation, Ishikawa (JP)

(72) Inventors: Yuji Haruki, Ishikawa (JP); Ikumi Arai, Ishikawa (JP); Naoaki Hirata, Ishikawa (JP); Yoichi Ueda, Ishikawa (JP); Tomoharu Yachikami, Ishikawa (JP)

(73) Assignee: EIZO Corporation, Ishikawa (JP)

( * ) Notice: Subject to any disclaimer, the term of this patent is extended or adjusted under 35 U.S.C. 154(b) by 110 days.

(21) Appl. No.: 16/486,996

(22) PCT Filed: Jan. 10, 2018

(86) PCT No.: PCT/JP2018/000228
§ 371 (c)(1),
(2) Date: Aug. 19, 2019

(87) PCT Pub. No.: WO2018/154981
PCT Pub. Date: Aug. 30, 2018

(65) Prior Publication Data
US 2020/0020306 A1  Jan. 16, 2020

(30) Foreign Application Priority Data
Feb. 21, 2017  (JP) .............................. JP2017-029877

(51) Int. Cl.
*G09G 5/38*  (2006.01)
*G09G 5/08*  (2006.01)
(Continued)

(52) U.S. Cl.
CPC ................. *G09G 5/38* (2013.01); *G06T 3/40* (2013.01); *G09G 5/08* (2013.01); *G09G 5/373* (2013.01);
(Continued)

(58) Field of Classification Search
CPC ..... G09G 2340/045; G09G 2340/0464; G09G 2354/00; G09G 2380/08; G09G 5/08;
(Continued)

(56) References Cited

U.S. PATENT DOCUMENTS

2013/0287313 A1   10/2013  Marchessoux et al.
2018/0300035 A1*  10/2018  Kaptelinin .......... G06F 3/04883

FOREIGN PATENT DOCUMENTS

JP    2015-198783 A    11/2015
JP    2016-168293 A     9/2016
WO    2012/085163 A1    6/2012

OTHER PUBLICATIONS

International Search Report dated Mar. 27, 2018 in corresponding International Application No. PCT/JP2018/000228; 1 pg.

\* cited by examiner

*Primary Examiner* — Xiao M Wu
*Assistant Examiner* — Scott E Sonners
(74) *Attorney, Agent, or Firm* — Maier & Maier, PLLC

(57) ABSTRACT

Provided are an image processing apparatus, a program and an image processing method capable of avoiding interference with the function of another program. An image processing apparatus includes a position information detection unit configured to detect position information indicating a position on a display, a region position setting unit configured to set the position of the region of interest on the display based on the position information, and an image processing unit configured to perform image process on at least one image among an image inside of the region of interest and an image outside of the region of interest. The region position setting unit, when the position information is changed with the image process, sets the position of the region of interest based on the position information immediately before the change.

10 Claims, 12 Drawing Sheets

(51) Int. Cl.
*G09G 5/373* (2006.01)
*G06T 3/40* (2006.01)

(52) U.S. Cl.
CPC ............ *G06T 2207/20104* (2013.01); *G09G 2340/045* (2013.01); *G09G 2340/0464* (2013.01); *G09G 2354/00* (2013.01); *G09G 2380/08* (2013.01)

(58) Field of Classification Search
CPC .. G09G 5/373; G09G 5/38; G09G 2340/0492; G09G 2320/0666; G09G 2340/0407; G09G 2340/14; G09G 2340/04; G09G 2320/06; G09G 2320/0606; G09G 2320/066; G09G 2320/0271; H04N 1/387; G06F 3/017; G06F 3/0416; G06F 3/0481; G06F 3/01; G06T 2200/24; G06T 11/60; G06T 11/20; G06T 3/40
See application file for complete search history.

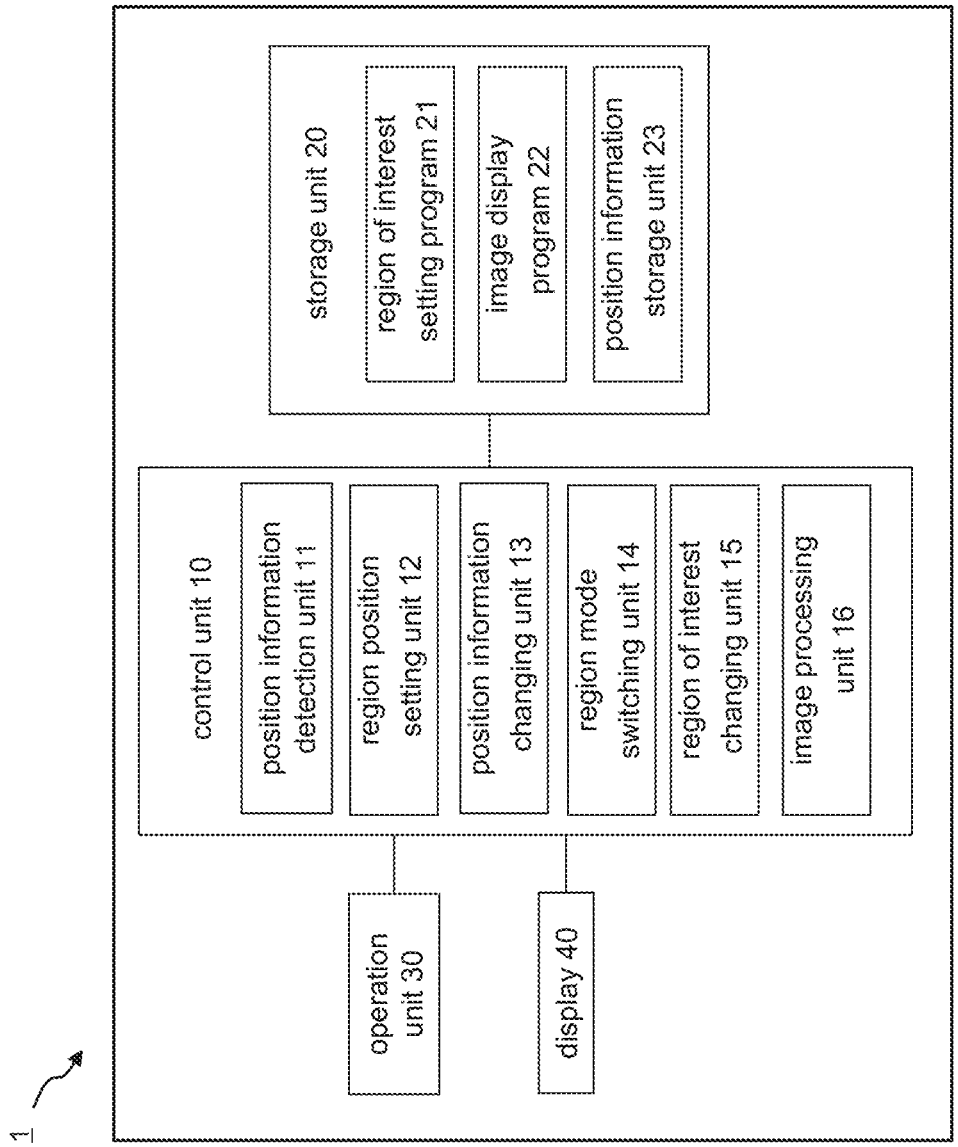
Fig. 2 FIRST EMBODIMENT

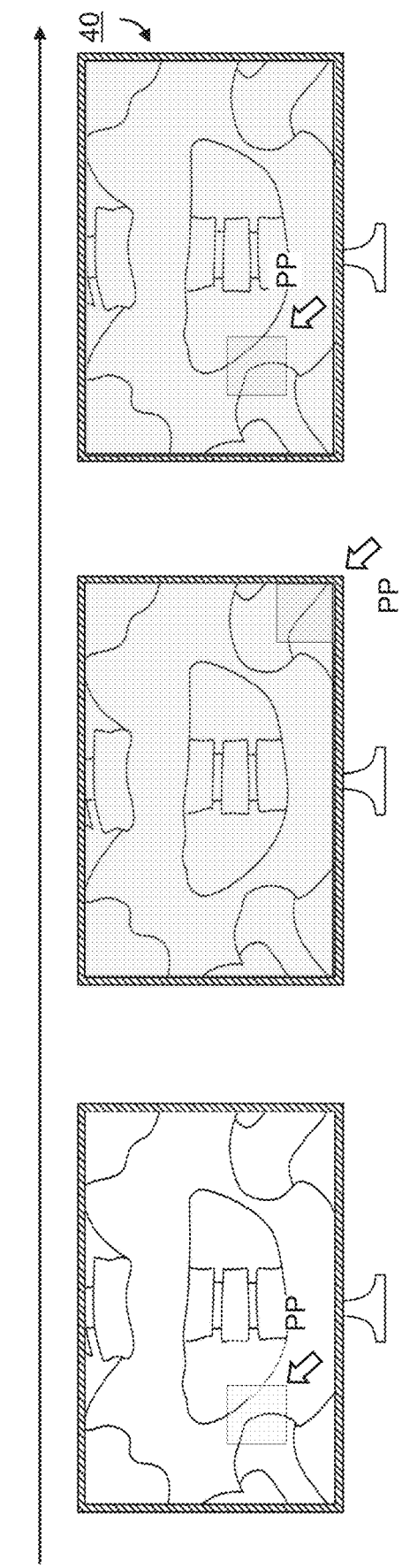

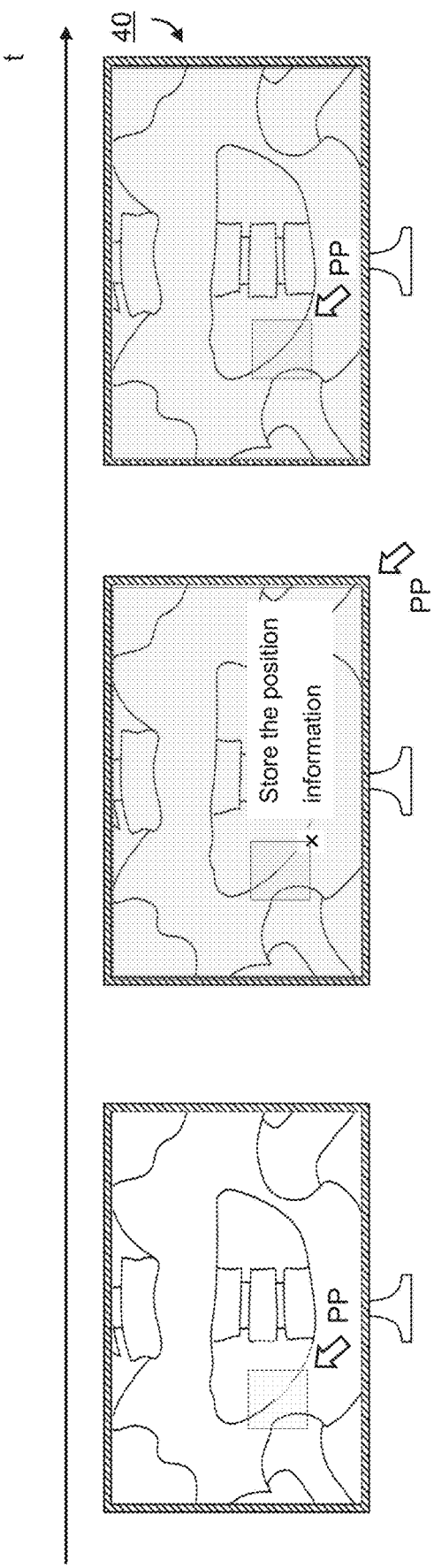

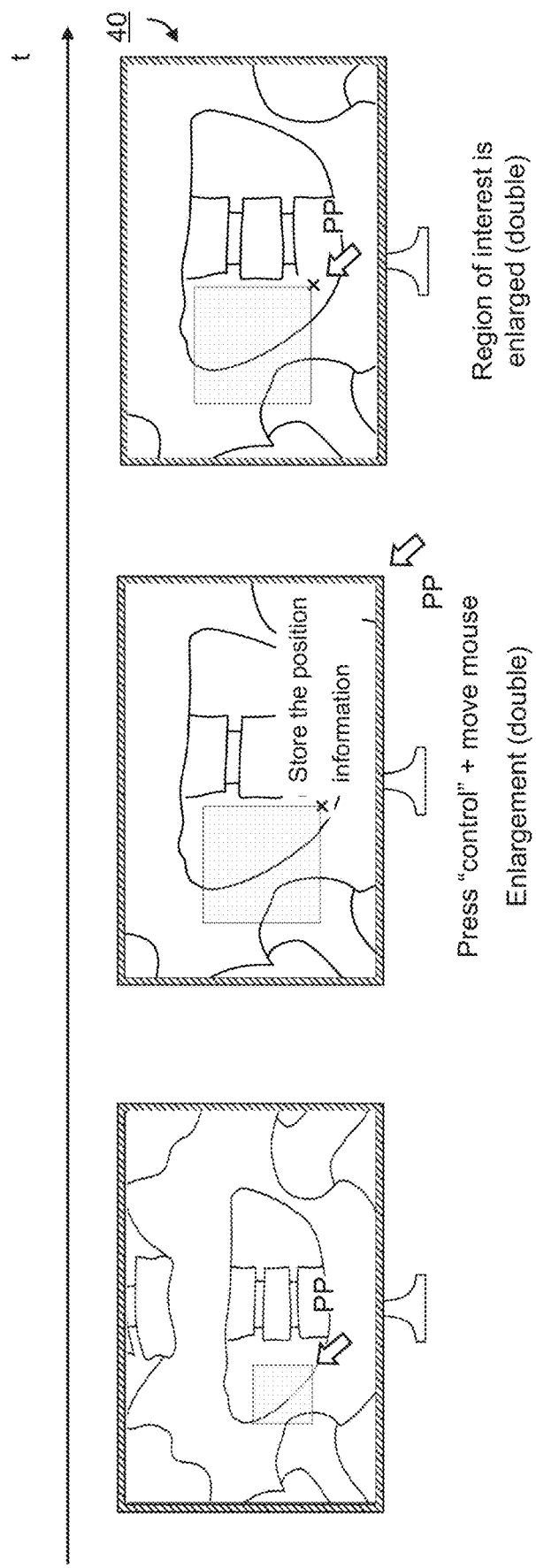

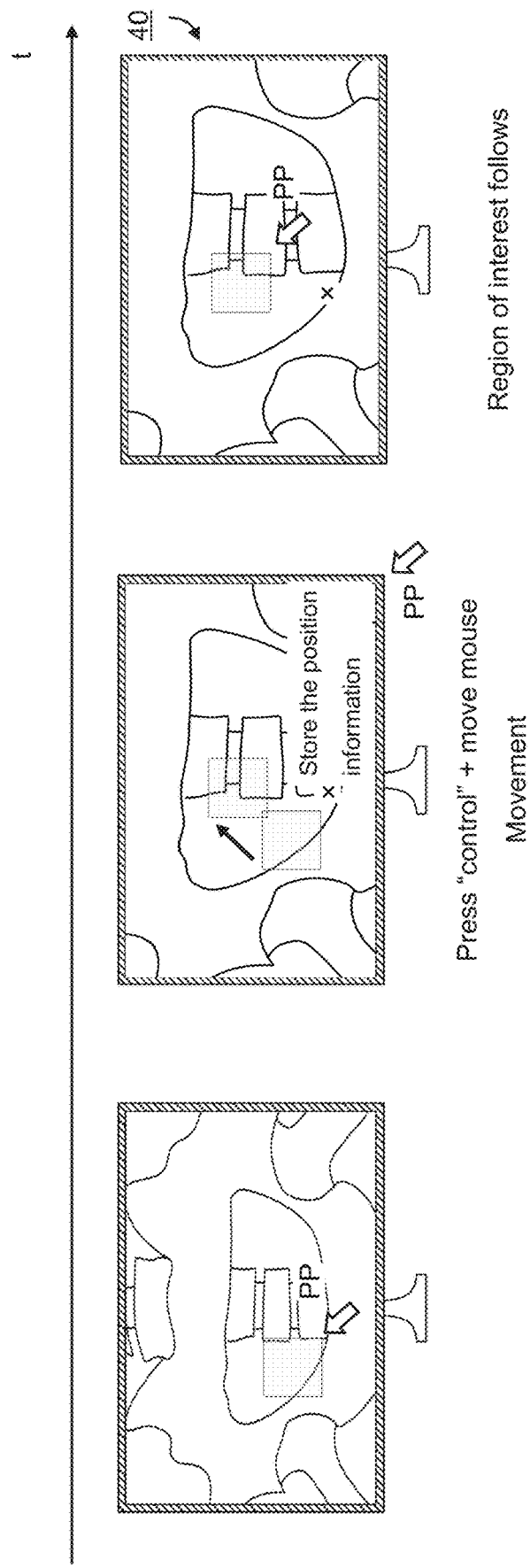

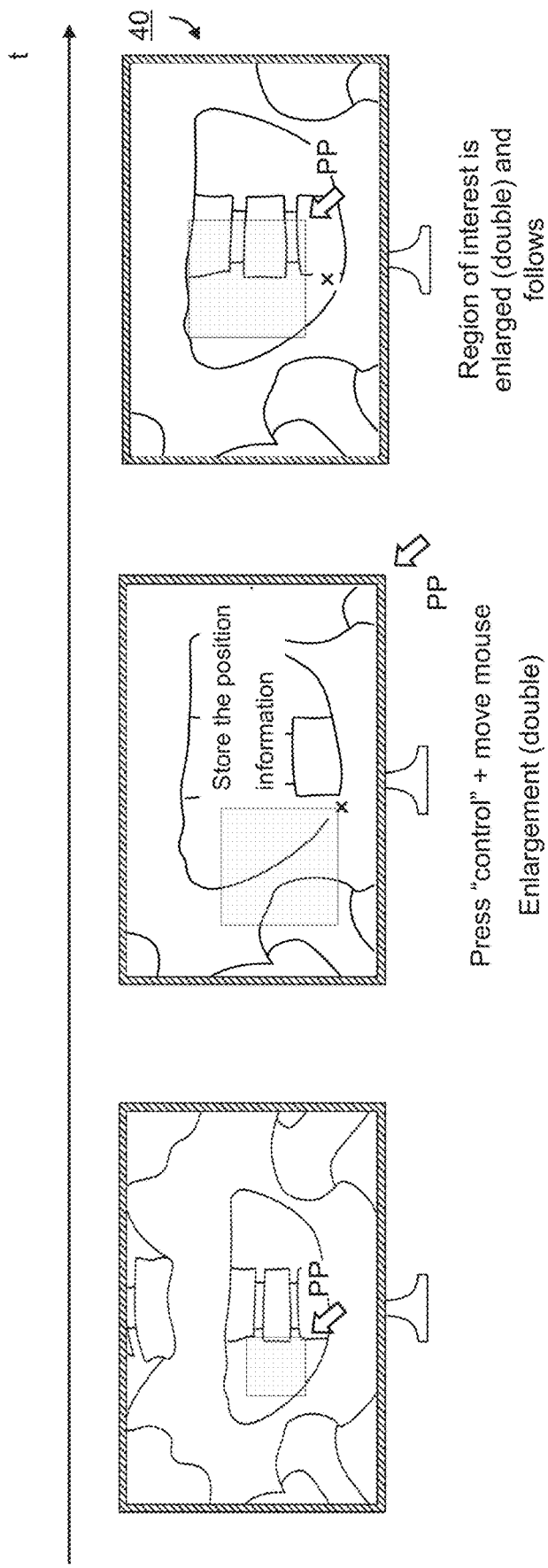

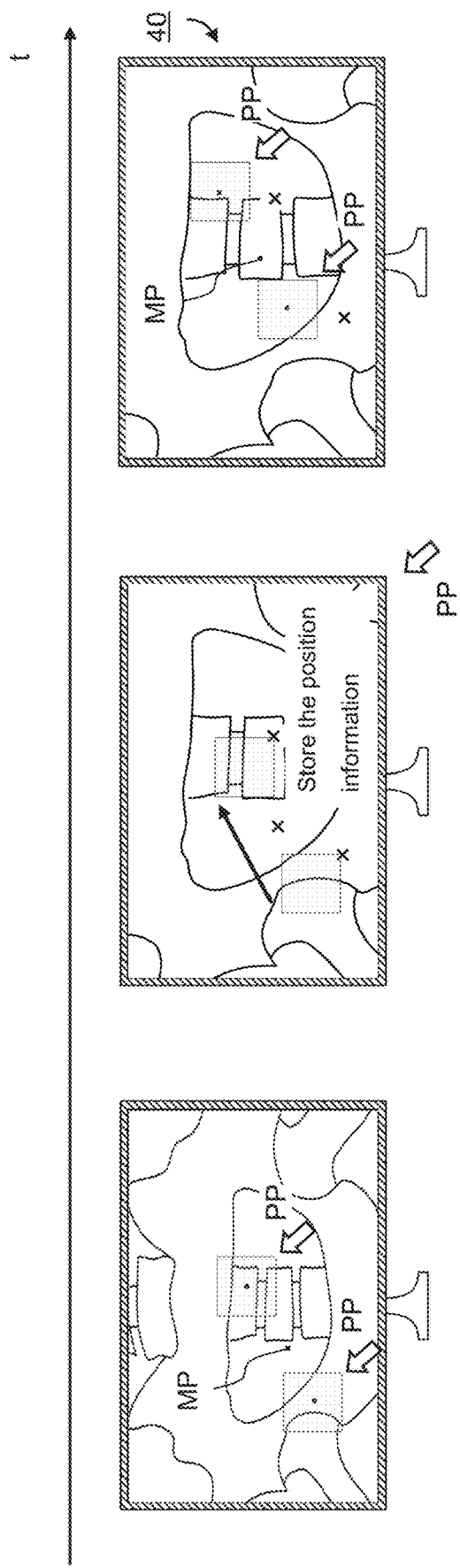

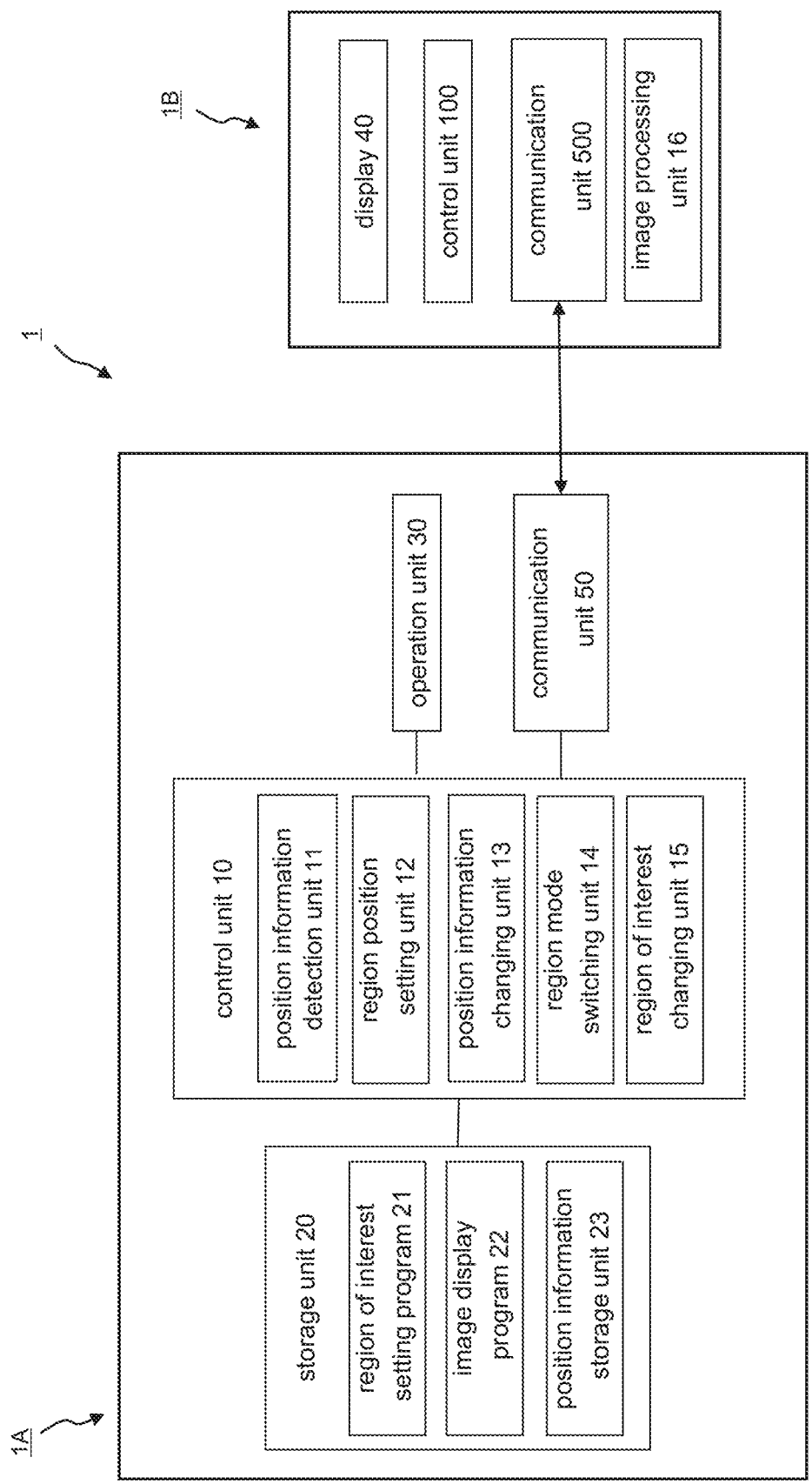

IMAGE PROCESSING APPARATUS, PROGRAM AND IMAGE PROCESSING METHOD

TECHNICAL FIELD

The present invention relates to an image processing apparatus, a program, and an image processing method.

BACKGROUND ART

An image processing apparatus has been put into practical, which sets a part of an image displayed on a monitor as a region of interest, and image processing is performed on an image inside or outside of the region of interest.

Patent Literature 1 discloses an image processing apparatus capable of highlighting a part of an image.

CITATION LIST

Patent Literature

[Patent Literature 1] WO 2012/085163

SUMMARY OF INVENTION

Technical Problem

By the way, various programs may be stored in the image processing apparatus. For example, a viewer for displaying a predetermined document may be stored. Here, when image processing is performed inside or outside of the region of interest, the functions of the image processing and the viewer interfere with each other depending on the viewer specifications, and the image may be displayed on the monitor in an undesirable way.

The present invention has been made in view of foregoing, and provides an image processing apparatus, a program, and an image processing method capable of avoiding interference with the function of another program.

Solution to Problem

The first aspect of present invention provides an image processing apparatus which includes a position information detection unit configured to detect position information indicating a position on a display, a region position setting unit configured to set the position of the region of interest on the display based on the position information, and an image processing unit configured to perform image process on at least one image among an image inside of the region of interest and an image outside of the region of interest. The region position setting unit, when the position information is changed with the image process, sets the position of the region of interest based on the position information immediately before the change.

According to the present invention, the region position setting unit is configured to set, when the position information is changed with the image process, the position of the region of interest based on the position information immediately before the change. This makes it possible to maintain the display state immediately before the position information is changed.

Various embodiments of the present invention will be illustrated below. The embodiments below can be combined with one another.

Preferably, the position information is specified by a pointer position of a pointer displayed on the display, and the region position setting unit sets a position associated with the pointer position as the position of the region of interest.

Preferably, the image processing apparatus further includes a position information changing unit configured to change the position information to a predetermined position when the image process is performed. The region position setting unit sets, even if the position information is changed, the position information immediately before the change as the position of the region of interest after the change.

Preferably, the image processing unit is configured to enlarge the region of interest when performing the image process.

Preferably, the image processing unit is configured to move the region of interest when performing the image process.

Preferably, the image processing unit is configured to perform the enlargement or the movement while maintaining the relative position of the region of interest in the entire image displayed on the display.

Preferably, the image processing unit performs image process to maintain the image quality of at least one image among an image inside of the region of interest and an image outside of the region of interest.

Preferably, the image processing unit is configured to hide the region of interest when performing the image process.

Preferably, the image processing apparatus includes a main unit and a display unit, the main unit and the display unit are configured to be communicable, the main unit includes the position information detection unit and the region position setting unit, and the display unit includes the display and the image processing unit.

The second aspect of present invention provides a program for causing a computer to function as a position information detection unit configured to detect position information indicating a position on a display, a region position setting unit configured to set the position of the region of interest on the display based on the position information, and an image processing unit configured to perform image process on at least one image among an image inside of the region of interest and an image outside the region of interest. The region position setting unit, when the position information is changed with the image process, sets the position of the region of interest based on the position information immediately before the change.

The third aspect of present invention provides an image process method includes a position information detection step of detecting, by a position information detection unit, position information indicating a position on a display, a region position setting step of setting, by a region position setting unit, the position of the region of interest on the display based on the position information, and an image processing step of performing, by an image processing unit, image process on at least one image among an image inside of the region of interest and an image outside of the region of interest. The region position setting unit, when the position information is changed with the image process, sets the position of the region of interest based on the position information immediately before the change.

FIG. 2 is a functional block diagram of the image processing apparatus 1.

FIGS. 5A to 5C are drawings showing process in a comparative example.

FIGS. 6A to 6C are drawings showing process in the image processing apparatus 1 according to an embodiment of the present invention.

FIGS. 7A to 7C are drawings showing the enlargement of a region of interest ROI with enlargement of an image.

FIGS. 8A to 8C are drawings showing the movement of a region of interest ROI with enlargement of an image.

FIGS. 9A to 9C are drawings showing enlargement and movement of a region of interest ROI with enlargement of an image.

FIGS. 10A to 10C are drawings explaining the behavior when a plurality of regions of interest ROI is set.

FIG. 12 is a functional block diagram of an image processing apparatus 1 configured by a main unit 1A and a display unit 1B.

DESCRIPTION OF EMBODIMENTS

Hereinafter, embodiments of the present invention will be described using the drawings. The various features shown in the embodiments described below can be combined with one another.

1. First Embodiment

Figure 1:
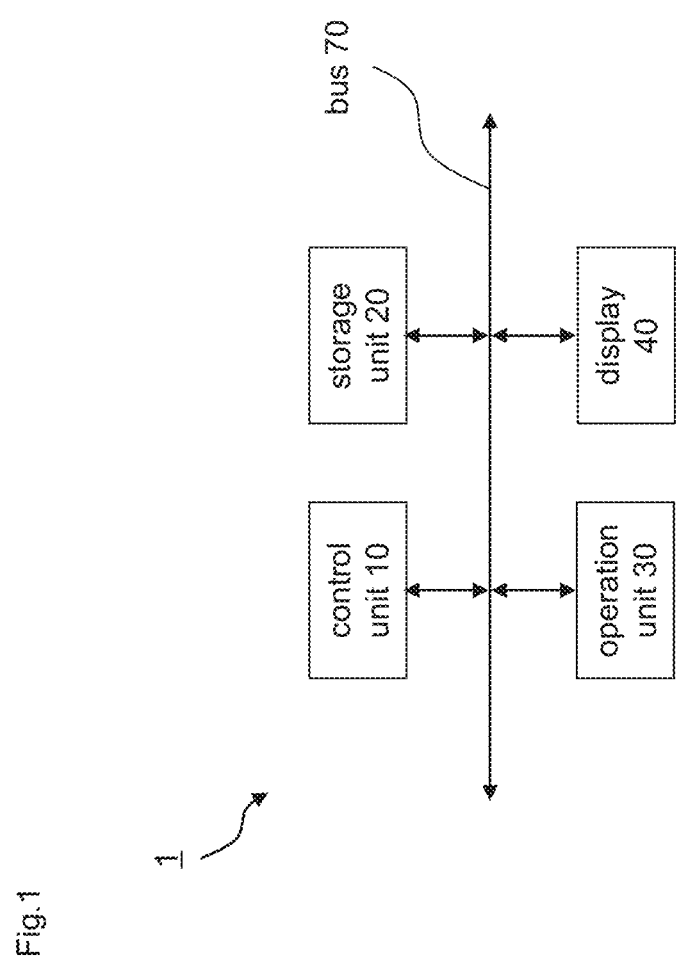
FIG. 1 is an exemplary block diagram of an image processing apparatus 1 according to an embodiment of the present invention.

As shown in FIGS. 1 and 2, an image processing apparatus 1 according to the first embodiment of the present invention is, for example, a single information processing apparatus, and includes a control unit 10, a storage unit 20, an operation unit 30, and a display 40. The control unit 10 is, for example, a CPU or the like and reads out the program stored in the storage unit 20 and executes various arithmetic processing. The storage unit 20 is, for example, a memory, an HDD, or an SSD and stores various data and programs. Here, the program may be pre-installed at the time of shipment of the image processing apparatus 1, may be downloaded as an application from a site on the Web, and may be transferred from another information processing apparatus or recording medium by wired or wireless communication. The operation unit 30 is, for example, a mouse, a keyboard, a touch panel, a touch pad, a motion recognition apparatus using a camera or the like, a voice input unit or the like and operates the image processing apparatus 1. The display 40 is, for example, a liquid crystal display, an organic EL display, a touch panel display, an electronic paper or other displays and displays various images (including still images and moving images). The bus 70 is, for example, a serial bus, a parallel bus or the like, and electrically connects the respective parts to enable transmission and reception of various data.

<Image Processing Apparatus 1>

As shown in FIG. 2, the control unit 10 of the image processing apparatus 1 includes a position information detection unit 11, a region position setting unit 12, a position information changing unit 13, a region mode switching unit 14, a region of interest changing unit 15, and image processing unit 16. The storage unit 20 includes a region of interest setting program 21, an image display program 22, and a position information storage unit 23.

The position information detection unit 11 detects position information indicating the position on the display 40. In the present embodiment, the position information is specified by a pointer position PP of a pointer displayed on the display 40. Here, the pointer can be moved to any position by a user operating the operation unit 30. In the present embodiment, the position corresponding to the tip of the pointer specifies the coordinates of position information.

When the position information is changed with the image processing by the image processing unit 16, the region position setting unit 12 sets the position of a region of interest ROI on the display 40 based on the position information immediately before the change. Here, the region of interest ROI is a region which is highlighted in the image displayed on the display 40 and is set by operating the operation unit 30.

The position information changing unit 13 changes the position information to a predetermined position when the image processing is performed. Then, while the image process is performed, that is, even when the position information is changed, the position immediately before the change is set as the position of the region of interest ROI. This is a specification of the image display program 22 and is performed in consideration of the relationship with other processes.

The region mode switching unit 14 switches the display mode of the region of interest ROI. The display mode of the region of interest ROI will be described later with reference to FIGS. 3 and 4.

The image processing unit 16 performs image process on at least one image among an image inside of the region of interest and an image outside of the region of interest ROI. For example, the image processing unit 16 performs image process for enhancing the gradation of the image in the region of interest ROI and image process suitable for grayscale to improve the visibility of the region of interest ROI. Also, conversely, the image processing unit 16 may perform process to lower the gradation of the image outside of the region of interest ROI and image process not suitable for grayscale to relatively improve the visibility of the region of interest ROI. The image processing unit 16 can also perform image process on images both inside and outside of the region of interest ROI. Further, the image processing unit 16 may enlarge the image in the region of interest ROI and display the enlarged image overlapped on the image outside of the region of interest ROI.

The region of interest setting program 21 realizes a function of the image processing apparatus 1 for setting the region of interest ROI. Control of the region of interest ROI is realized by the cooperation of the region of interest setting program 21, the position information detection unit 11, the region position setting unit 12, the region mode switching unit 14, the region of interest changing unit 15 and the image processing unit 16.

The image display program 22 realizes a function for controlling the image processing apparatus 1 and displaying a predetermined image on the display 40. In the present embodiment, the image display program 22 is a viewer for displaying a predetermined document. Further, the image display program 22 corresponds to a program for changing the pointer position to a predetermined position when the pointer is not displayed. When the image display program 22 cooperates with the position information changing unit 13 and the image processing unit 16, the image process by the image processing unit 16 and the display function by the image display program 22 may interfere with each other. Such interference will be described later using FIG. 5A.

The position information storage unit 23 stores the position information. In the present embodiment, the position information storage unit 23 stores the pointer position PP operated by the operation unit 30. Such storage may be performed every predetermined time or every predetermined movement amount of the pointer.

<Region of Interest ROI>

Figure 3A:
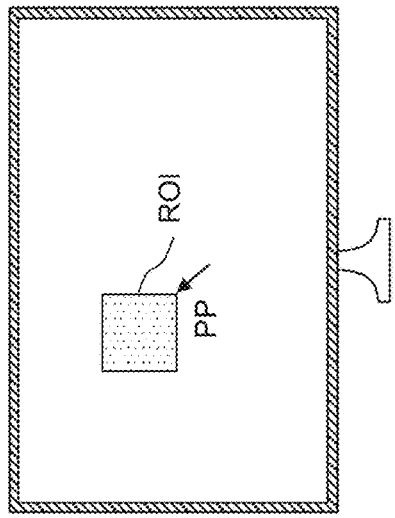
FIGS. 3A to 3D are conceptual drawings of various aspects of a region of interest ROI.
Figure 3B:
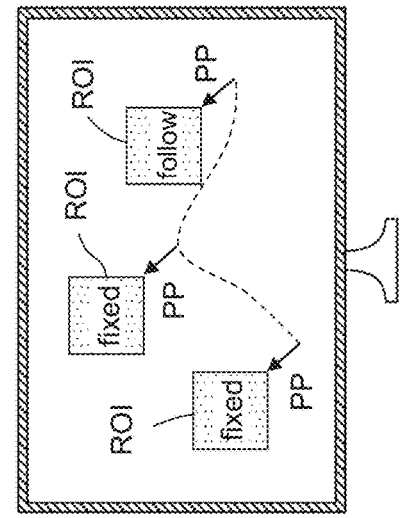
Figure 3C:
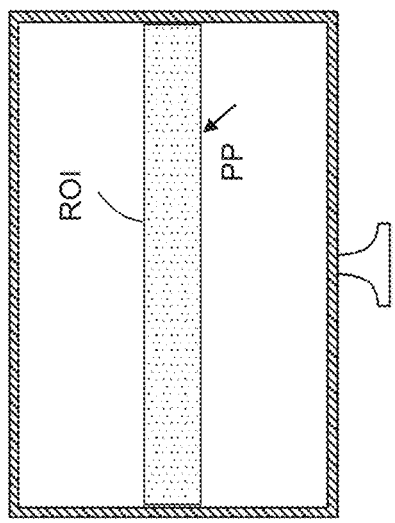
Figure 3D:
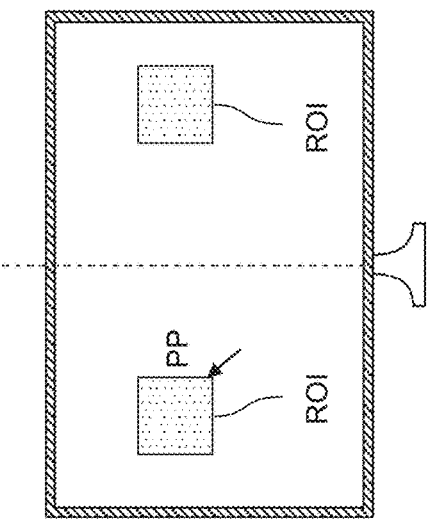
Figure 4B:
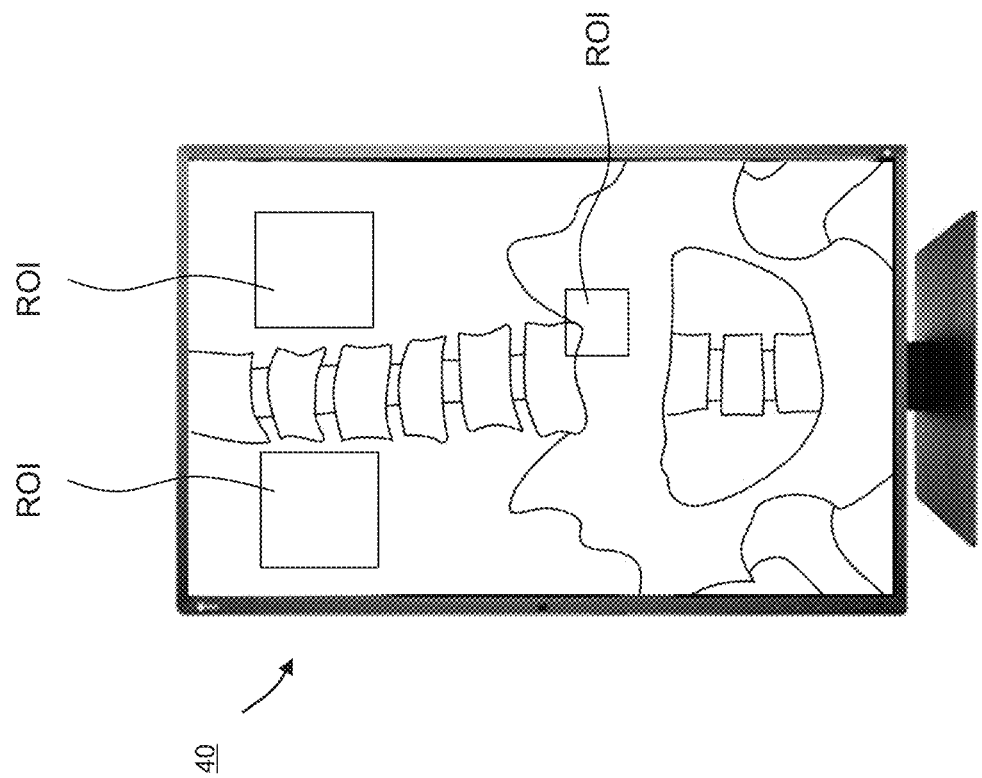
FIGS. 4A and 4B illustrate a state of setting a region of interest ROI in an image. Here, FIG. 4A corresponds to FIG. 3B and FIG. 4B corresponds to FIG. 3D.

Next, the region of interest ROI will be described using FIGS. 3 and 4. Here, the arrow in the drawing represents a pointer, and the same in the subsequent drawings. The region of interest ROI is set based on the position information. FIG. 3A is an aspect in which the region of interest ROI is displayed in a band shape over the entire width of the display 40. The user moves the pointer using the operation unit 30, and sets the position associated with the pointer position PP as the region of interest ROI. In the example of FIG. 3A, the region of interest ROI can be set in a band shape across the entire width of the display 40 from the coordinates corresponding to the pointer position PP. FIG. 3B is an aspect in which the region of interest ROI is displayed in a rectangular shape. The user can move the pointer using the operation unit 30, generate a rectangle of a predetermined size from the coordinates corresponding to the pointer position PP, and set the region of interest ROI. FIG. 3C shows an aspect in which the region of interest ROI is displayed in a rectangular shape at a position symmetrical with respect to the center of the display 40. For example, in an X-ray image etc., it is used when confirming substantially symmetrical images of human lungs. In the example of FIG. 3C, when one of the regions of interest ROI is specified, a position symmetrical with the pointer position PP is calculated, and the other region of interest ROI is set. FIG. 3D shows an aspect of setting a plurality of regions of interest ROI. The region of interest ROI can be fixed by moving the pointer using the operation unit 30 and executing a "fix" instruction at a place where the user wants to fix the region of interest ROI. Also, after the region of interest ROI is fixed, the newly generated region of interest ROI can be made to follow the movement of the pointer. Here, the shape of the region of interest ROI is arbitrary and may be of any size and shape, such as a rectangle, a polygon, a circle, an ellipse, a star, or the like. Further, the position associated with the pointer position PP is not limited to the tip of the pointer and may be an arbitrary point within a predetermined range from the tip of the pointer.

These display modes can be switched by the region mode switching unit 14. Here, the height of the band in FIG. 3A and the size of the rectangle in FIGS. 3B to 3D can be changed to any size by the operation unit 30.

Figure 4A:
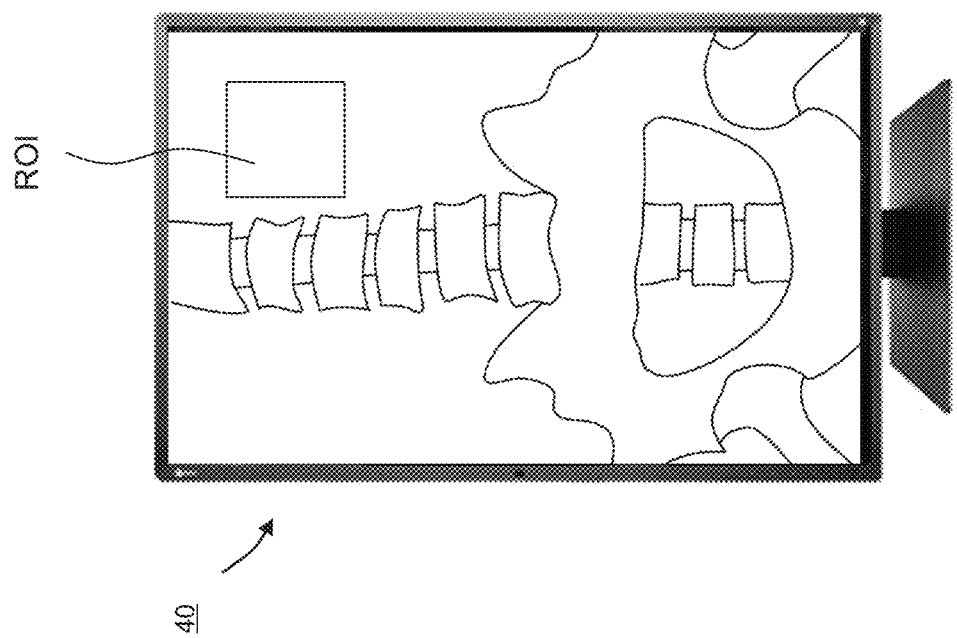

FIG. 4A illustrates a state of setting the region of interest ROI in an actual image and corresponds to the rectangular display in FIG. 3B. Also, FIG. 4B corresponds to the multiple display of FIG. 3D. In this way, highlighting the region of interest ROI improves the visibility of the image in the region of interest ROI.

<Control of ROI>

Next, control of the region of interest ROI will be described with reference to FIGS. 5 to 10. FIGS. 5A to 5C are comparative examples of the present invention, and the region position setting unit 12 is configured to set the region of interest ROI based on current position information (i.e. pointer position PP). FIGS. 6A to 6C show an embodiment of the present invention, which, when the position information is changed with image process, sets the position of the region of interest ROI based on the position information immediately before the change. Here, in the present embodiment, according to the specifications of the image display program 22, the pointer is not displayed during execution of the image process, and the pointer position PP is changed. In other words, in the present embodiment, the position of the region of interest ROI when the pointer is not displayed is set based on the position information immediately before the pointer is not displayed. Here, t in the drawing represents time, which means that time passes in the direction of the arrow. That is, time passes in the order of FIG. 5A to FIG. 5C. Also, the highlighted portion in the drawing represents the region of interest ROI, and the same in the subsequent drawings.

Comparative Example 1

As shown in FIG. 5A, the region position setting unit 12 sets the position of the region of interest ROI based on the current pointer position PP and highlights the region.

In this state, it is assumed that the gradation of the entire image shown in FIG. 5A is to be increased. In one example, according to the specification of the image display program 22, the gradation of the entire image is enhanced while the command "shift+control+up arrow" is pressed by the keyboard as the operation unit 30. Further, as shown in FIG. 5B, according to the specification of the image display program 22, the pointer is not displayed while that command is pressed. When the pointer is not displayed, the position information changing unit 13 changes the pointer position PP to a predetermined position according to the specifications of the image display program 22. In the example of FIG. 5B, the lower right of the display 40 corresponds to a predetermined position. Then, with the movement of the pointer position PP, the position of the region of interest ROI is changed. That is, since the region position setting unit 12 is configured to set the position of the region of interest ROI based on the current pointer position PP, as shown in FIG. 5B, the region of interest ROI is set at the lower right position which is changed by the position information changing unit 13. Although the user intends to use the position shown in FIG. 5A as the region of interest ROI, the specification of the image display program 22 causes a problem that the position of the region of interest ROI during the gradation change is unintentionally changed.

Thereafter, when pressing the command "shift+control+up arrow" by the keyboard is finished, the pointer is redisplayed as shown in FIG. 5C. At this time, according to the specifications of the image display program 22, when the pointer is displayed again, the pointer position PP is returned to the position immediately before the pointer becomes not displayed. As a result, the region of interest ROI returns to the state of FIG. 5A.

On the other hand, in the image processing apparatus 1 according to an embodiment of the present invention, such problem is solved. In the example of FIGS. 6A to 6C, the region position setting unit 12 sets the position of the region of interest ROI when the pointer is not displayed, based on the position information (pointer position PP) immediately before the pointer becomes not displayed. The details are described below.

As shown in FIG. 6A, the region position setting unit 12 sets the position of the region of interest ROI based on the current pointer position PP and highlights the region. This is the same as the comparative example 1.

In this state, it is assumed that the operation to increase the gradation of the entire image shown in FIG. 6A is performed. At this time, the position information changing unit 13 changes the pointer position PP to a predetermined position. In the present embodiment, when the pointer is not displayed, the control unit 10 stores the position information (pointer position PP) immediately before the pointer becomes not displayed in the position information storage unit 23. This is a feature of the present embodiment.

Then, when the pointer is not displayed, the region position setting unit 12 is configured to set the pointer position PP immediately before the pointer becomes not displayed as the position information of the region of interest ROI when the pointer is not displayed. This is also a feature of the present embodiment. Therefore, even if the pointer position PP is changed while the pointer is not displayed, the region position setting unit 12 can set the pointer position PP immediately before the pointer becomes not displayed as the position of the region of interest ROI when the pointer is not displayed.

Thereafter, when the operation of changing the gradation is completed, the pointer is redisplayed as shown in FIG. 6C. At this time, according to the specification of the image display program 22, the position information changing unit 13 returns the pointer position PP to the position immediately before the pointer becomes not displayed. This is the same as the comparative example 1.

As described above, in the present embodiment, when the pointer is not displayed, the region of interest ROI is not set based on the current position information of the pointer, but is set based on the position information immediately before the pointer becomes not displayed. For this reason, even when using the image display program 22 which is designed to move the region of interest ROI to another position when the pointer is not displayed, it is suppressed that the region of interest ROI is unintentionally changed.

Next, other image process on an image in the region of interest ROI will be described using FIGS. 7 to 10. It is assumed that the enlargement operation for enlarging the entire image shown in FIG. 7A is started. In one example, according to the specifications of the image display program 22, the image is enlarged continuously or stepwise when the mouse is moved while "control" is pressed on the keyboard as the operation unit 30. As shown in FIG. 7B, the control unit 10 stores position information (pointer position PP), immediately before the enlargement operation is started and the pointer becomes not displayed, in the position information storage unit 23.

When the pointer is not displayed, the region position setting unit 12 sets the pointer position PP immediately before the pointer becomes not displayed as the position information of the region of interest ROI when the pointer is not displayed. In addition, the region of interest ROI is enlarged when the pointer is not displayed. Here, in the present embodiment, the enlargement ratio is assumed to be double. Then, the size of the region of interest ROI is enlarged double in accordance with the enlargement ratio (double) of the image. Such enlargement is performed by the region of interest changing unit 15. Thereby, all or most of the images included in the region of interest ROI before enlargement become included in the region of interest ROI after enlargement. Further, the enlargement is controlled so that the image included in the region of interest ROI before the enlargement become as close as possible to the center of the display 40. Such control is realized by using known pattern matching or feature vectors. Therefore, it is possible to omit the procedure of the user operating the operation unit 30 for changing the size of the region of interest ROI.

Thereafter, when the command that "control" is pressed on the keyboard with mouse operation is finished, the pointer is redisplayed as shown in FIG. 7C. At this time, according to the specification of the image display program 22, when the pointer is redisplayed, the pointer position PP is returned to the position immediately before the pointer becomes not displayed.

On the other hand, in the example of FIG. 8, the region of interest ROI is moved when the pointer is not displayed. That is, the position of the region of interest ROI during the enlargement operation is moved in the direction of the arrow based on the pointer position PP before enlargement and the image process. Such movement is performed by the region of interest changing unit 15. For example, the image in the region of interest ROI before enlargement is compared with the image after enlargement by a known image tracking process using pattern matching or feature vectors. And then, the region of interest ROI is moved toward a portion corresponding to the image in the region of interest ROI before enlargement. At this time, image tracking process using pattern matching or feature vectors is performed in consideration of the enlargement ratio of the image.

In the examples of FIGS. 7 and 8, it is preferable that the relative position of the region of interest ROI in the entire image displayed on the display 40 is maintained before and after enlargement.

These processes can be combined with one another. For example, as shown in FIG. 9, when the pointer is not displayed, the region of interest ROI which is doubled in size may be moved toward the location corresponding to the image in the region of interest ROI before enlargement.

Next, process in the case that a plurality of regions of interest ROI is set will be described. As shown in FIG. 10, when there are two regions of interest ROI and when the pointers are not displayed, the two position information (pointer position PP) immediately before the pointers become not displayed, are stored in position information storage unit 23. At the same time, the coordinates of the midpoint MP of the line connecting the centers of the two regions of interest ROI (black points in FIGS. 10A and 10C) are stored in the position information storage unit 23. Then, enlargement of the image is controlled so that the midpoint MP is at the center of the image after the enlargement. At this time, the pointer position PP is moved in the direction of the arrow while maintaining the relative position with respect to the midpoint MP. At the same time, the region of interest ROI is displayed at the position designated by the pointer position PP. Also, in the example of FIG. 10, the enlargement of the region of interest ROI may be performed.

By the various processes described above, interference between the function of the image display program 22 and the region of interest setting program 21 is avoided. Further, before and after image process by the image processing unit 16, the position of the region of interest ROI can be fixed or moved to a preferable position, and the region of interest ROI can be enlarged as needed.

<Region of Interest ROI when Executing P by P Function>

Figure 11A:
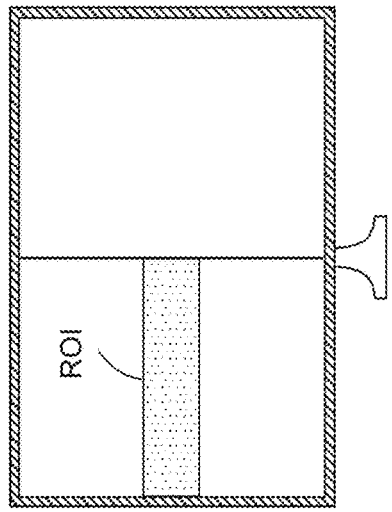
FIGS. 11A and 11C are drawings showing a state in which a region of interest ROI is displayed on the entire screen when two screens by the P by P function are displayed.
Figure 11B:
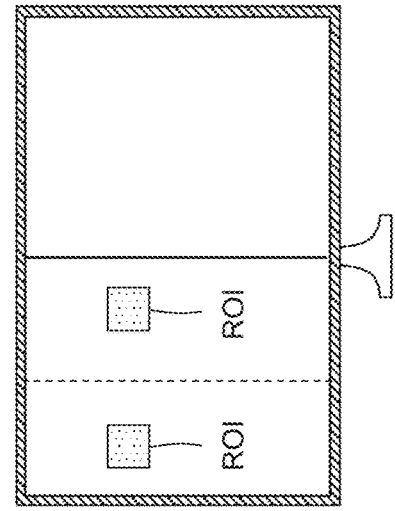
FIGS. 11B and 11D are drawings showing a state in which the region of interest ROI is displayed each two screens.
Figure 11C:
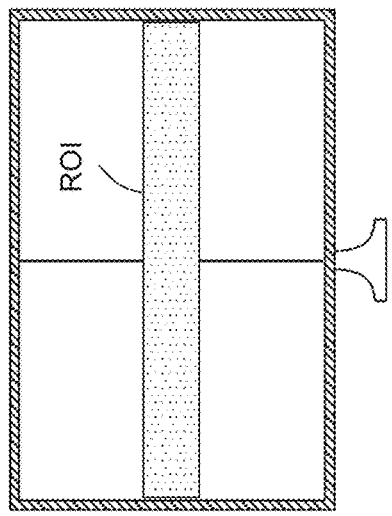
Figure 11D:
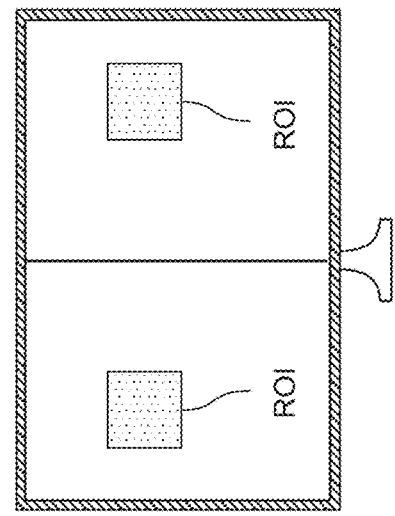

Next, the region of interest ROI at the time of execution of the P by P function will be described using FIGS. 11A to 11D. FIG. 11A corresponds to FIG. 3A and FIG. 11C corresponds to FIG. 3C. As shown in FIGS. 11A and 11C, the region of interest ROI can be displayed on the entire display in the case that two screens are displayed by the P by P function. Further, as shown in FIGS. 11B and 11D, the region of interest ROI may be displayed on each of the two screens. These can be switched by the region mode switching unit 14.

2. Second Embodiment

An image processing apparatus 1 according to the second embodiment of the present invention will be described with reference to FIG. 12. The image processing apparatus 1 according to this embodiment includes a main unit 1A and a display unit 1B that can communicate with each other, which is a main difference from the first embodiment. In other words, the image processing apparatus 1 in the second embodiment can be regarded as a system including the main unit 1A and the display unit 1B. The following description will be focused on differences from the first embodiment.

The main unit 1A includes a communication unit 50 in addition to the units which are included in the first embodiment. The communication unit 50 transmits and receives various data to and from the display unit 1B or another information processing apparatus. The communication unit 50 is an arbitrary I/O device. The display unit 1B is, for example, a monitor, and includes a display 40, a control unit 100, a communication unit 500, and an image processing unit 16. The control unit 100 corresponds to the control unit 10 in the main unit 1A, and the communication unit 500 corresponds to the communication unit 50 in the main unit 1A. Also, the image processing unit 16 is provided in at least one of the main unit 1A or the display unit 1B. In the present embodiment, the image processing unit 16 is provided in the display unit 1B.

In the second embodiment, the communication unit 50 of the main unit 1A and the communication unit 500 of the display unit 1B are configured to communicate information with each other. Further, image data is transmitted from the communication unit 50 to the communication unit 500.

The communication unit 50 transmits the position information (pointer position PP) of the region of interest ROI to the communication unit 500. Then, the image processing unit 16 performs highlighting process on the image in the region of interest ROI based on the position information (pointer position PP).

If the image processing unit 16 is provided in the main unit 1A, the communication unit 50 transmits the image data after highlighting process to the communication unit 500 of the display unit 1B in addition to the position information (pointer position PP) of the region of interest ROI.

Another Embodiment

As mentioned above, although various embodiments were described, the image processing apparatus 1 according to this invention is not limited to these.

In the above description, the aspect in which the pointer is not displayed during execution of the image process has been described, but the present invention is not limited to this. For example, if the touch panel in which the pointer is not displayed is used as the display 40, the position of the region of interest ROI is set by the touch operation by the user. Then, if image process is performed on at least one image among an image inside of the region of interest and an image outside of the region of interest ROI, for example, by swipe operation or the like, and the position information is changed with image process, the position of the region of interest ROI may be set based on the position information immediately before the change. In another example, it is assumed that the finger of the user has left the touch panel after the position of the region of interest ROI is set by the touch operation. In this case, although the position information detection unit 11 does not detect the position information, the image processing apparatus 1 may store the position information detected just before. And if the image process is performed in this state, the position information stored just before is changed with the image process. At this time, the position of the region of interest ROI may be set based on the position information immediately before the change.

Further, the display mode may be switchable to display an image conforming an image quality "DICOM" or "CAL1." which is a standard established in the medical image field. In this case, the image quality of the region of interest ROI may be maintained when the pointer is redisplayed after not being displayed. That is, before and after the image process by the image processing unit 16, the display mode of the image quality in the region of interest ROI is maintained.

Further, the image processing unit 16 can be configured to hide the region of interest ROI when the pointer is not displayed. At this time, if necessary, the region of interest ROI may be redisplayed when the pointer is redisplayed, and the region of interest ROI may be enlarged or moved at the same time.

Further, when the position information is changed with the image process, the position information may be in a predetermined range from the pointer position PP immediately before the change, instead of the position information immediately before the change. Also, the pointer position PP at a predetermined time before the pointer becomes not displayed may be used. For example, the position information stored immediately before in the storage unit 20 or the position information stored two or three times before may be used. Further, among the pointer positions PP within a predetermined time before becoming not displayed, the pointer position PP that stays for the longest time may be used.

Further, the enlargement operation of the image may be performed based simply on the center of the image displayed on the display 40.

Further, the present invention can also be provided as a computer readable non-transitory recording medium in which the functions of the image processing apparatus 1 are implemented. In addition, programs for realizing these functions can be distributed via the Internet or the like. In addition, the respective units constituting the image processing apparatus 1, the main unit 1A, and the display unit 1B may be included in the same casing or may be distributed and arranged in a plurality of casings.

Further image processing method may be provided. The image processing method includes a position information detection step of detecting, by a position information detection unit, position information indicating a position on a display, a region position setting step of setting, by a region position setting unit, the position of the region of interest on the display based on the position information, and an image processing step of performing, by an image processing unit, image process on at least one image among an image inside of the region of interest and an image outside of the region of interest. The region position setting unit, when the position information is changed with the image process, sets the position of the region of interest based on the position information immediately before the change.

Further, a shortcut for switching display or non-display of the region of interest ROI may be assigned. In this case, the control unit 10 may determine whether the image display program 22 doesn't use the same shortcut.

1: image processing apparatus
1A: main unit
1B: display unit
10, 100: control unit
11: position information detection unit
12: region position setting unit
13: position information changing unit
14: region mode switching unit 15: region of interest changing unit
16: image processing unit
20: storage unit
21: region of interest setting program
22: image display program
23: position information storage unit
30: operation unit
40: display
50, 500: communication unit

The invention claimed is:

1. An image processing apparatus comprising:
a position information detection unit; a region position setting unit; a position information changing unit; and an image processing unit; wherein
the position information detection unit is configured to detect position information indicating a position on a display,
the region position setting unit is configured to set a position of a region of interest on the display based on the position information,
the image processing unit is configured to perform image processing on at least one image among an image inside of the region of interest and an image outside of the region of interest,
the image processing performed by the image processing unit includes at least one of first and second image processing,
the first processing is a processing for enhancing a gradation of the image,
the second processing is a processing for enlarging the image,
the position information changing unit is configured to change the position information to a predetermined position when the image processing is performed,
the position information is specified by a pointer position of a pointer displayed on the display; and
the region position setting unit sets, even if the position information is changed to the predetermined position with the image processing, the position of the region of interest after the position information is changed to the position of the region of interest immediately before the position information is changed.

2. The image processing apparatus of claim 1, wherein the region position setting unit sets a position associated with the pointer position as the position of the region of interest.

3. The image processing apparatus of claim 1, wherein the image processing unit is configured to enlarge the region of interest when performing the image process.

4. The image processing apparatus of claim 3, wherein the image processing unit is configured to perform the enlargement of the region of interest while maintaining the relative position of the region of interest in the entire image displayed on the display.

5. The image processing apparatus of claim 1, wherein the image processing unit is configured to move the region of interest when performing the image process.

6. The image processing apparatus of claim 5, wherein the image processing unit is configured to perform the movement of the region of interest while maintaining the relative position of the region of interest in the entire image displayed on the display.

7. The image processing apparatus of claim 1, wherein the image processing unit performs image process to maintain the image quality of at least one image among an image inside of the region of interest and an image outside of the region of interest.

8. The image processing apparatus of claim 1, wherein the image processing unit is configured to hide the region of interest when performing the image process.

9. A computer readable non-transitory recording medium storing a program for causing a computer to function as:
a position information detection unit configured to detect position information indicating a position on a display;
a region position setting unit configured to set a position of a region of interest on the display based on the position information; and
an image processing unit configured to perform image processing on at least one image among an image inside of the region of interest and an image outside the region of interest;
a position information changing unit configured to change the position information to a predetermined position when the image processing is performed;
wherein
the image processing performed by the image processing unit includes at least one of first and second image processing,
the first processing is a processing for enhancing a gradation of the image,
the second processing is a processing for enlarging the image,
the position information is specified by a pointer position of a pointer displayed on the display; and
the region position setting unit sets, even if the position information is changed to the predetermined position with the image processing, the position of the region of interest after the position information is changed to the position of the region of interest immediately before the position information is changed.

10. An image process method comprising:
a position information detection step of detecting, by a position information detection unit, position information indicating a position on a display;
a region position setting step of setting, by a region position setting unit, a position of a region of interest on the display based on the position information; and
an image processing step of performing, by an image processing unit, image processing on at least one image among an image inside of the region of interest and an image outside of the region of interest;
a position information changing step of changing the position information to a predetermined position when the image processing is performed; and
wherein
the image processing performed by the image processing unit includes at least one of first and second image processing,
the first processing is a processing for enhancing a gradation of the image,
the second processing is a processing for enlarging the image,
the position information is specified by a pointer position of a pointer displayed on the display; and
in region position setting step, the region position setting unit sets, even if the position information is changed to the predetermined position with the image processing, the position of the region of interest after the position information is changed to the position of the region of interest immediately before the position information is changed.

* * * * *